(12) United States Patent
Baldus et al.

(10) Patent No.: US 7,978,063 B2
(45) Date of Patent: Jul. 12, 2011

(54) WIRELESS NETWORK HAVING BODY COUPLED COMMUNICATION FOR MOBILE PATIENT MONITORING

(75) Inventors: Heribert Baldus, Aachen (DE); Martin J. Elixmann, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 798 days.

(21) Appl. No.: 11/720,892

(22) PCT Filed: Dec. 5, 2005

(86) PCT No.: PCT/IB2005/054063
§ 371 (c)(1),
(2), (4) Date: Jun. 5, 2007

(87) PCT Pub. No.: WO2006/064397
PCT Pub. Date: Jun. 22, 2006

(65) Prior Publication Data
US 2009/0231125 A1    Sep. 17, 2009

Related U.S. Application Data (60) Provisional application No. 60/635,645, filed on Dec. 13, 2004, provisional application No. 60/670,386, filed on Apr. 12, 2005.

(51) Int. Cl.
*G08B 1/08* (2006.01)
*H04B 7/15* (2006.01)
*A61B 5/00* (2006.01)
(52) U.S. Cl. .................. 340/539.12; 455/11.11; 600/309
(58) Field of Classification Search ............ 340/539.12, 340/10.1, 870.07
See application file for complete search history.

(56) References Cited

U.S. PATENT DOCUMENTS

| | | | |
|---|---|---|---|
| 5,796,827 | A | 8/1998 | Coppersmith et al. |
| 5,914,701 | A | 6/1999 | Gersheneld et al. |
| 6,211,799 | B1 | 4/2001 | Post et al. |
| 6,223,018 | B1 | 4/2001 | Fukumoto et al. |
| 6,287,252 | B1 | 9/2001 | Lugo |

(Continued)

FOREIGN PATENT DOCUMENTS
DE      10233071 B4    2/2004

OTHER PUBLICATIONS

R. Shepherd, Bluetooth wireless technology in the home, Oct. 2001, Electronics and Communication Engineering Journal, 197.*

(Continued)

*Primary Examiner* — Benjamin C Lee
*Assistant Examiner* — Cal Eustaquio (57) ABSTRACT

A wireless network for monitoring a patient (10) comprises at least one wearable monitor (12, 70) including a physiological condition sensor (34, 74) coupled to the patient (10) to sense and communicate data related to one physiological function of the patient (10). A first body communication unit (16, 78) interfaces with the at least one wearable monitor (12, 70) to communicate over the patient (10) utilizing a near field capacitive body coupled protocol. A relay system (14, 50 72) includes a second body communication unit (18, 52, 80) that receives data from the at least one wearable monitor (12, 70) and communicates with the first body communication unit (16, 78) utilizing the near field capacitive body coupled protocol. An external communication unit (22) communicates the data to a remote medical monitoring station via a cell phone network or the internet.

17 Claims, 6 Drawing Sheets

U.S. PATENT DOCUMENTS

| | | | |
|---|---|---|---|
| 6,602,469 B1* | 8/2003 | Maus et al. | 422/68.1 |
| 7,542,721 B1* | 6/2009 | Bonner et al. | 455/41.2 |
| 2001/0001237 A1* | 5/2001 | Stroda et al. | 340/573.4 |
| 2002/0013538 A1* | 1/2002 | Teller | 600/549 |
| 2003/0052770 A1* | 3/2003 | Mansfield et al. | 340/310.01 |
| 2003/0125017 A1* | 7/2003 | Greene et al. | 455/414 |
| 2003/0144581 A1* | 7/2003 | Conn et al. | 600/309 |
| 2004/0027244 A9* | 2/2004 | Menard | 340/573.1 |
| 2006/0001550 A1* | 1/2006 | Mann et al. | 340/870.07 |

OTHER PUBLICATIONS

Hachisuka, K., et al.; Development and Performance Analysis of an Intra-Body Communication Device; 2003; IEEE Int'l. Conf. Solid State Sensors, Actuators and Microsystems; pp. 1722-1725.

Handa, T., et al.; A Very Low-Power Consumption Wireless ECG Monitoring System Using Body as a Signal Transmission Medium; 1997; IEEE Inn Conf. on Solid-State Sensors and Actuators; pp. 1003-1006.

Kunze, C., et al.; Application of Ubiquitous Computing in Personal Health Monitoring Systems; http://www.ibt.etec.uni-karlsruhe.de/bmt2002/paper/1199.pdf.

Paradiso, R.; Wearable Health Care System for Vital Signs Monitoring; http://www.wealthy-ist.com/uploads/itab2003_paradiso.pdf.

Rubel, P., et al.; Beyond EPI-MEDICS; 2004; 2nd OpenECG Workshop; Berlin, Germany; pp. 75-76.

* cited by examiner

WIRELESS NETWORK HAVING BODY COUPLED COMMUNICATION FOR MOBILE PATIENT MONITORING

CROSS REFERENCE TO RELATED APPLICATIONS

This application claims the benefit of U.S. provisional application Ser. No. 60/635,645 filed Dec. 13, 2004 and U.S. provisional application Ser. No. 60/670,386 filed Apr. 12, 2005, which are both incorporated herein by reference.

The following relates to wireless body networks. It finds particular application with alarm relaying from one or more wireless sensors to a cellular phone and further to a surveillance and/or alarm center. However, it is to be appreciated that the invention may also find application in providing communication between wireless sensors and other wireless transponders capable of receiving near field body coupled communication technology.

Patients are typically monitored of one or more physiological functions when they receive medical attention at a medical facility. For example, it may be desirable to monitor heart function, pulse, blood pressure, blood oxygen level and the like. Conventionally, such monitoring is accomplished utilizing sensors wired to various output devices that can notify medical personnel of one or more conditions. Alternatively, wireless sensors can be employed with wireless networks to transmit such data to one or more wireless transponders such as a display, a monitor, memory, central terminal and the like.

Such sensors typically provide continuous monitoring of a particular physiological function and an alarm output if a critical event arises. The alarm output can be transmitted utilizing conventional communication technology such as a wired hospital network, radio frequency, Bluetooth or magnetic coupling (B-field), for example. However, when the patient ranges beyond the controlled medical facility communication environment, conventional communication technologies can become unreliable. While a cell phone provides a convenient communication link between a patient and a remote site, direct communication by the monitor in an emergency is more awkward. An ECG monitor can be directly wired to a cell phone, but positioning wires is inconvenient and the wires interfere with normal usage of the cell phone. Cell phones are often compatible with Bluetooth communication protocols. However, in some situations, body attenuation prevents proper signal propagation. For example, if a patient falls down (e.g., due to a heart attack) and covers the chest mounted ECG system, the Bluetooth communication is heavily attenuated by the body and typically disrupted.

Magnetic coupling communications signals travel readily through the body but consume excessive amounts of energy restricting portability. Due to the weight of batteries, carrying a large battery power supply is inconvenient. In addition, magnetic coupling is typically unidirectional which does not accommodate bidirectional verification routines.

Typically, communication between the wireless sensor and the mobile phone is fixed due to static configured connectivity. Such static configuration prevents the safe and flexible connection to other nearby mobile phones in an emergency when the primary mobile phone is unavailable. Furthermore, such fixed association inhibits the systems from working reliably in multi-user scenarios.

The present invention contemplates an improved apparatus and method that overcomes the aforementioned limitations and others.

According to one aspect, a wireless network for monitoring a patient comprises at least one wearable monitor including a physiological condition sensor coupled to the patient to sense and communicate data related to one physiological function of the patient. A first body communication unit interfaces with the at least one wearable monitor to communicate over the patient utilizing a near field capacitive body coupled protocol. A relay system includes a second body communication unit that receives data from the at least one wearable monitor and communicates with the first body communication unit utilizing the near field capacitive body coupled protocol. An external communication unit communicates the data to a remote medical monitoring station.

According to another aspect, a method for communicating medical information within a wireless network includes monitoring a physiological condition of a patient via a sensor coupled to the patient. Data related to one physiological function of the patient is communicated from the sensor via a first body communication unit that interfaces with the at least one wearable monitor to communicate over the patient utilizing a near field capacitive body coupled protocol. The data is relayed to a mobile alarm relay system from the wearable monitor via a second body communication unit that receives data from the at least one wearable monitor and communicates with the first body communication unit utilizing the near field capacitive body coupled protocol. The data is communicated from the mobile alarm relay system to a remote medical monitoring station.

According to yet another aspect, a method for transmitting medical information within a wireless network includes associating a wearable monitor with a mobile alarm relay system including initializing communication between a first body communication unit associated with the wearable monitor and a second body communication unit associated with the mobile alarm relay system utilizing a near field capacitive body coupled protocol. Secure communication is established between the wearable monitor and the mobile alarm relay system by sending an authentication request from the wearable monitor to the mobile alarm relay system and returning an authentication key from the mobile alarm relay system to the wearable monitor. Communication between the wearable monitor and the mobile alarm relay system is verified to be active by monitoring the connection between the wearable monitor and the mobile alarm relay system, and generating an alarm if the connection becomes inactive. An alarm is triggered if the data transmitted by the wearable monitor is outside of a predetermined threshold including transmitting an alarm message from the wearable monitor to the mobile alarm relay system, and relaying the alarm message from the mobile alarm relay system to an external network.

One advantage of the present invention is that it facilitates transmission of medical information in an emergency to a patient monitoring station.

Another advantage is that out-patient monitored medical information is automatically communicated to the patient's medical care professionals.

Another advantage is that medical information can be relayed to a wireless transponder without risk of attenuation caused by the patient.

Another advantage is that medical information can be redundantly communicated to insure that such information is received by a wireless transponder.

Another advantage resides in enabling patient monitors to interconnect with and use existing cell phone networks to communicate medical information.

Another advantage is that patients who need constant medical monitoring can move freely throughout the community.

Numerous additional advantages and benefits will become apparent to those of ordinary skill in the art upon reading the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
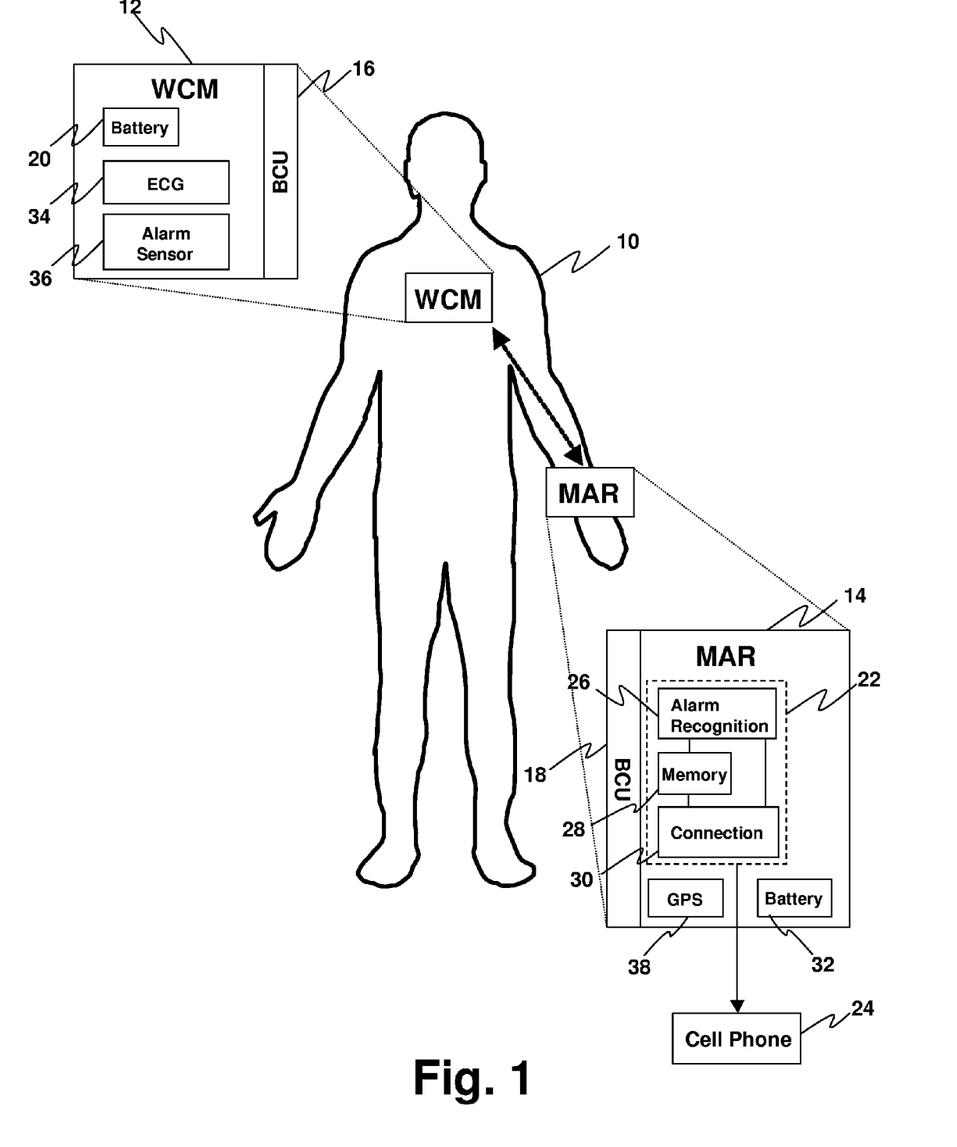
FIG. 1 illustrates a body coupled communication network that includes a wireless sensor that communicates to one or more external devices via a mobile alarm relay component.

A patient 10 is equipped with one or more wearable monitors, such as a wearable electrocardiographic (ECG) monitor (WCM) 12, and a mobile alarm relay system (MAR) 14 (e.g., mobile phone, PDA or other device which connects to wireless networks), which is utilized to forward alarms generated by the wearable monitor 12 to an external entity. It is to be appreciated that the wearable monitor 12 can be employed to monitor any physiological function related to the patient 10. Both the wearable monitor 12 and the mobile alarm relay system 14 are equipped with a body communication unit (BCU) 16, 18. The BCUs 16, 18 communicate utilizing a near-field body-coupled communication technology, based on capacitive coupling.

The wearable monitor 12 is designed to be power efficient and use low energy consumption technologies so that it can be powered by a relatively small battery 20. The monitor communicates the monitored physiological condition to a remote monitoring station via an external connection device 22, e.g. the transmit/receive portion of a cell phone 24 that communicates with the cell phone network. The external connection device 22 includes an alarm recognition component 26 that determines if an alarm condition has been sensed by the wearable monitor 12. A memory 28 is employed by the alarm recognition component 26 to store monitor output before and after the alarm for subsequent retrieval. The memory 28 can store additional data sent by the wearable monitor 12 that relates to a particular physiological function of the patient 10. A connection component element 30 connects the mobile relay 14 to the cell phone 24.

The mobile relay 14 is preferably designed to be carried in contact or close proximity with a portion of the body, e.g. in a clothing pocket, or wrapped around the wrist, that can carry more weight, particularly a larger battery 32. In the preferred embodiment, the mobile alarm relay system 14 is a cell phone hand set that has been modified to include the BCU and other circuitry and has been appropriately programmed.

First, the BCUs 16, 18 are associated via body coupled communication. At this stage of communication, security can be set up and a shared authentication key can be exchanged among communication components. After initialization of the BCUs 16, 18 is complete, connections between the BCUs 16, 18 is established and communication can begin. Once communication is started, verification of the communication between the BCUs 16, 18 is monitored to insure that the communication remains active. If communication is inactive, an alarm can be triggered to notify the system of such communication failure.

The wearable monitor BCU 16 receives physiological information from an electrocardiograph (ECG) sensor 34 or other sensor(s). Optionally, an alarm sensor 36 determines if the output of the monitor calls for an alarm message to be issued. The alarm message is communicated via the wearable monitor BCU 16 to the mobile alarm relay system 14 for further relaying. Alternately, all monitored data can be transferred and the alarm recognition circuit 26 of the relay 14 can recognize the alarm condition rather than the alarm signal. In the preferred cell phone embodiment, the alarm signal causes the cell phone to dial a preselected telephone number to report the emergency. Preferably, the cell phone includes a GPS system 38 which communicates the stricken patient's location as well to medical professionals or emergency dispatchers at the receiving station.

Additionally, ECG data can be transferred to the mobile alarm relay system 14 with the alarm signal so that the remote receiving station can determine a plan of action based on such particularized data. For example, if the patient's pulse exceeds an alarm threshold, the caregiver can utilize such pulse data to determine the appropriate action to take when administering care to the patient 10. In another embodiment, the data is stored into the memory 28 in the mobile alarm relay system 14 or in the wearable monitor 12 so that data can be trended to determine the previous condition of the patient 10. In yet another embodiment, data can be downloaded on a periodic basis from the memory 28 to a remote processor for analysis.

Figure 2:
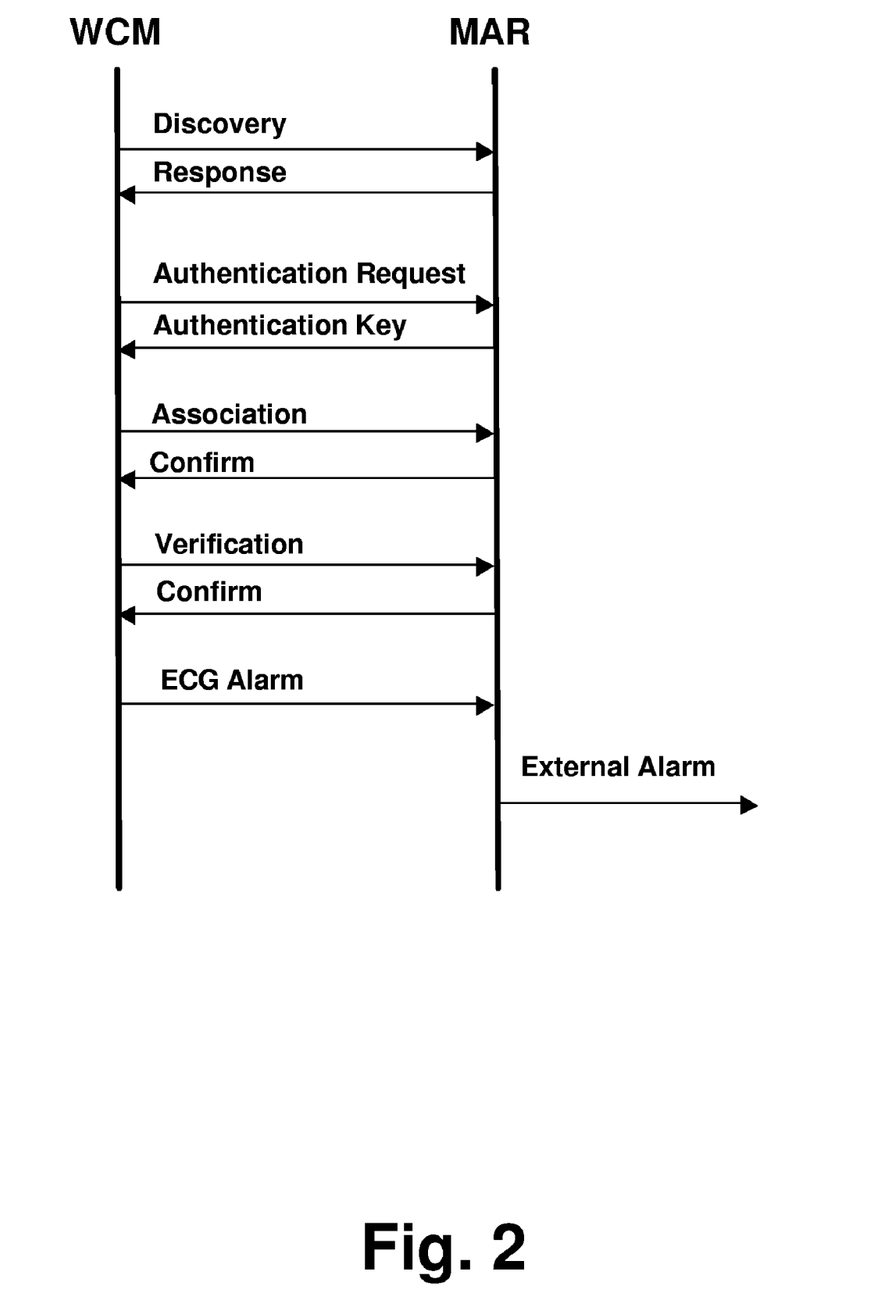
FIG. 2 illustrates a protocol employed in FIG. 1 to facilitate communication between the wireless sensor, the mobile alarm relay component and one or more external devices.

FIG. 2 illustrates the communication protocol between the wearable monitor 12 and the mobile alarm relay system 14 shown in FIG. 1. A body coupled communication protocol is employed to facilitate communication between the wearable monitor 12 and the mobile alarm relay system 14. Discovery of the wearable monitor 12 is accomplished by sending a discovery signal from the wearable monitor 12 to the mobile alarm relay system 14 once the wearable monitor 12 is introduced to the network (e.g., attached to the patient). A response signal is transmitted back to the wearable monitor 12 by the mobile alarm relay system 14. Security can be set up by exchanging a shared authentication key between the wearable monitor 12 and mobile alarm relay system 14. An authentication request is communicated from the wearable monitor 12 to the mobile alarm relay system 14 and an authentication key is returned by the mobile alarm relay system 14 to the wearable monitor 12. An association signal is sent from the wearable monitor 12 to the mobile alarm relay system 14 and the mobile alarm relay system 14 returns a confirm signal to verify establishment of a connection between the wearable monitor 12 and mobile alarm relay system 14 on the network.

Once communication is established, a verification signal is sent at various times from the wearable monitor 12 to the mobile alarm relay system 14. When a verification signal is received, the mobile alarm relay system 14 returns a confirm signal to indicate that communication is active between the wearable monitor 12 and the network. In case of an alarm detected by the wearable monitor 12, an alarm signal is transmitted from the wearable monitor 12 to the mobile alarm relay system 14. In one embodiment, data is also transmitted with the alarm signal to provide specific information relative to the alarm. The alarm signal is further transmitted from the mobile alarm relay system 14 to a remote receiving component (e.g., transponder) to trigger an external alarm. When there are a plurality of mobile monitors, analogous protocol is used each to establish communication with the mobile alarm relay system 14.

In FIG. 3, the patient 10 is again equipped with a wearable monitor 12 and an identification and relaying component (IRC) 50. The wearable monitor 12 and the relay 50 are each equipped with a body communication unit (BCU) 16, 52. The BCUs 16, 52 communicate utilizing a two-way near field body coupled communication technology, which is based on capacitive coupling with the patient's body. The wearable monitor BCU 16 receives alarm information from an electrocardiograph (ECG) sensor 34 detected by the wearable monitor 12. An alarm message is transferred from an alarm sensor 36 via the wearable monitor BCU 16 to the IRC 50 for further relaying.

Figure 3:
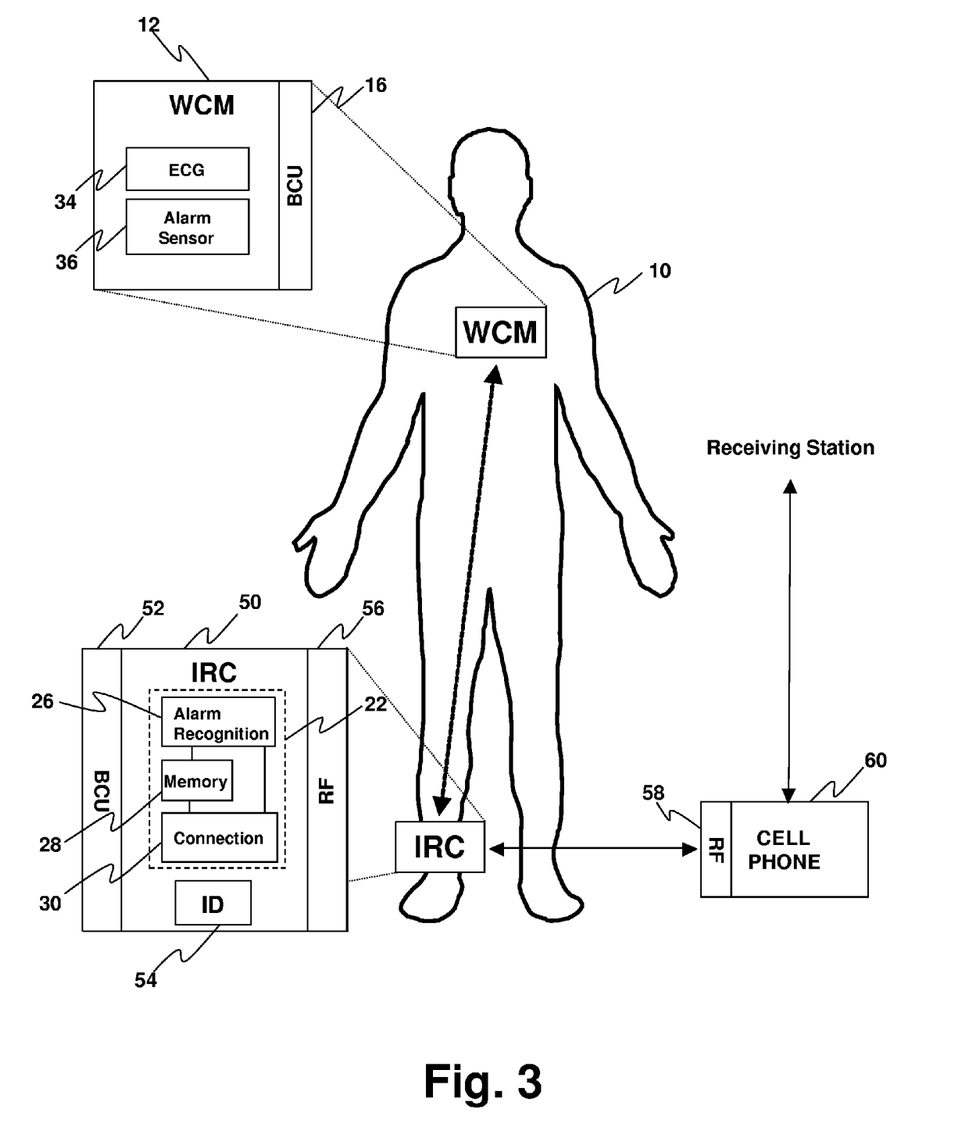
FIG. 3 illustrates a communication network that utilizes a body coupled communication technology and radio frequency technology to transmit information to an external network.

In contrast to the wearable monitor 12, which is located in close proximity to the heart, the IRC 50 can be placed on a part of the body with no risk of attenuation (e.g. arms or legs). The IRC 50 includes an identification (ID) component 54 that provides unique patient identification. The IRC 50 further includes an RF system 56 that transmits information for communication via an RF system 58 to a mobile alarm relay system, preferably a cellular phone 60, preferably using a Bluetooth or other short range, lower power transmission system. In turn, the cellular phone 60 relays data over the cell phone network to the medical professionals at a receiving station. Alternatively or additionally, the relay can communicate with a PC or PCA which communicates the alarm and other information over the Internet. Other network communications devices are also contemplated. In this manner, patient information gathered at one area of a patient's body can be communicated from a central location on the patient 10 to a global network.

An alarm recognition component 26 determines if an alarm has been sent by the wearable monitor 12. The memory 28 is employed by the alarm recognition component 26 to store alarms for subsequent retrieval. The memory 28 can store additional data sent by the wearable monitor 12 that relates to a particular physiological function of the patient 10. The connection element 30 connects the relay 50 to the cell phone 60. More specifically, the RF system 56 of the relay 60 interfaces to the external connection device, e.g., the transmit/receive portion of the cell phone to communicate through the cell phone network.

Figure 4:
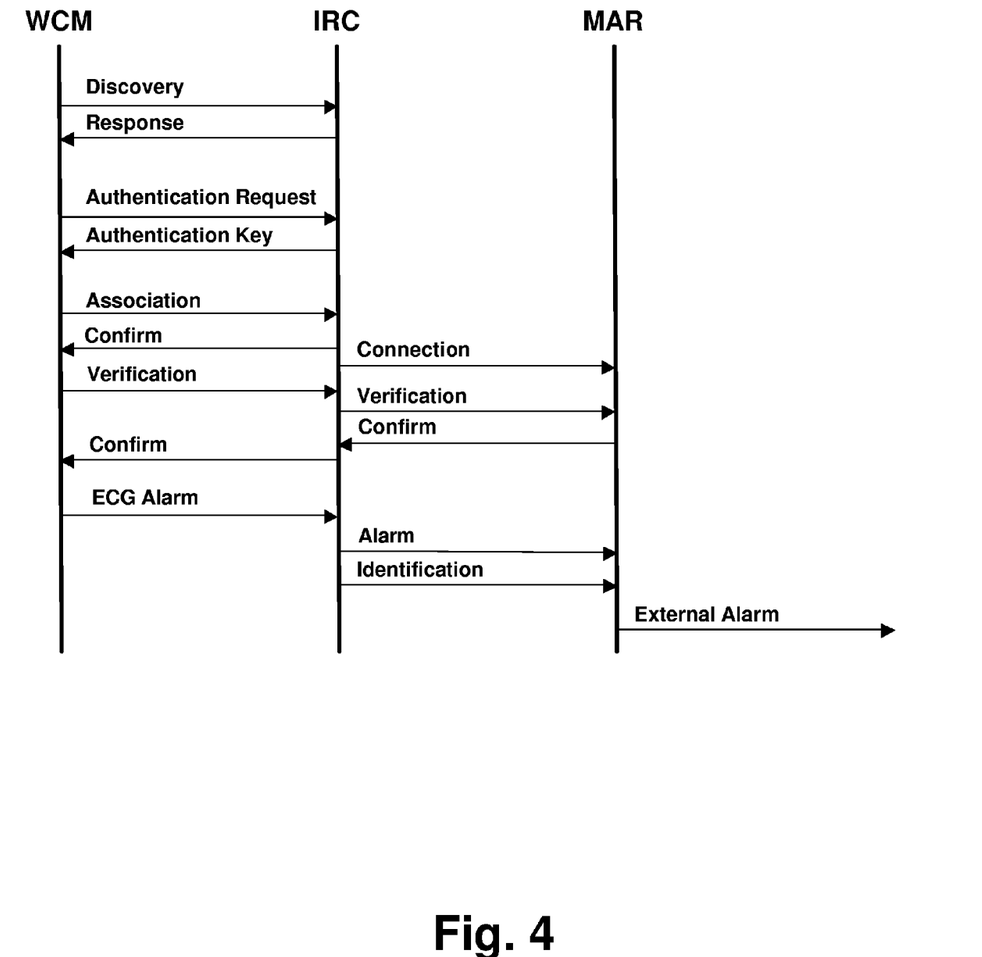
FIG. 4 shows a protocol employed in FIG. 3 to facilitate communication utilizing body coupled communication technology and radio frequency technology.

FIG. 4 illustrates the message flow between the wearable monitor 12, the relay 50 and the mobile alarm relay system or cell phone 60 of FIG. 3. Communication between the wearable monitor 12 and the relay 50 is facilitated via a body coupled communication technology. Communication between the relay 50 and the mobile alarm relay system or cell phone 38 is accomplished via radio frequency (RF) technology. Initially, the BCUs 16, 52 of the wearable monitor 12 and the relay 50 are discovered by the body coupled communication network. A discovery signal is sent from the wearable monitor 12 to the relay 50 which returns a response signal to the wearable monitor 12. Next, security is established by exchanging a shared authentication key between the wearable monitor 12 and the relay 50. The wearable monitor 12 sends an authentication request to the relay 50 and the relay 50 returns an authentication key to the wearable monitor 12. Finally, the connection between the BCUs 16, 52 of the wearable monitor 12 and relay 50 is established via the body coupled communication network. An association signal is sent from the wearable monitor 12 to the relay 50. The relay 50 returns a confirm signal to the wearable monitor 12 to verify that communication is established. Additionally, an RF connection between the relay 50 and the cell phone 60 is established after the relay 50 sends a connection signal to the cell phone 60.

The connection between the wearable monitor 12, the relay 50 and the cell phone 60 (mobile alarm relay system) is monitored and verified. The wearable monitor 12 sends a verification signal to the relay 50 and another verification signal is sent from the relay 50 to the cell phone 60 or other mobile alarm relay system. The cell phone 60 responds by sending a confirm signal to the relay 50. A confirm signal is also sent from the relay 50 to the wearable monitor 12. In this manner, the network is notified if a communication failure takes place. Once the communication between the wearable monitor 12, the relay 50 and the cell phone 60 is established, security is implemented and transmission and reception of signals is verified.

If the wearable monitor 12 detects an alarm, an ECG alarm signal is sent from the wearable monitor 12 to the relay 50. Afterward, an alarm signal and an alarm identification signal are sent from the relay 50 to the cell phone 60 or other mobile alarm relay system. After receiving the alarm and identification signals from the relay 26, the cell phone 60 sends an external alarm signal to the medical emergency receiving station.

Figure 5:
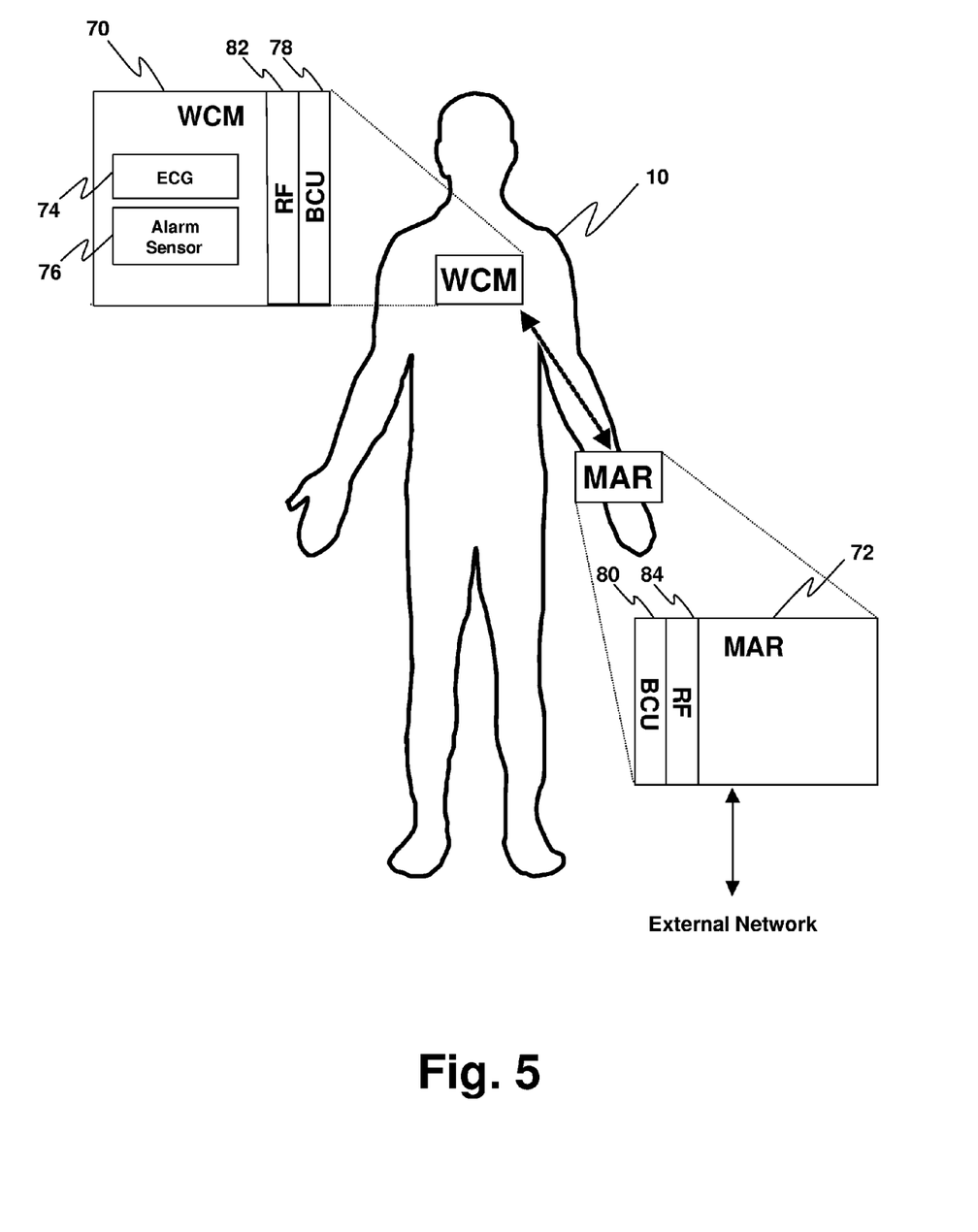
FIG. 5 shows a redundant communication network that employs both a body coupled communication technology and radio frequency technology to transmit information between a wireless sensor and relay component.

FIG. 5 illustrates a redundant communication system where the patient 10 is equipped with a wearable monitor (WCM) 70 and a mobile alarm relay system (MAR) 72, which is utilized for alarm forwarding to an external network. An ECG monitors 74 the patient's heart. Additionally or alternatively, an alarm sensor 76 monitors the second ECG or other physiological condition and determines when an alarm triggering aberration has occurred. Both the wearable monitor 70 and the relay system 72 are equipped with body communication units (BCUs) 78, 80 as well as with RF (e.g., Bluetooth) communication units 82, 84 for mutual peer-to-peer communication. In one embodiment, the relay system 72 is additionally equipped with cellular network connectivity, which is used for alarm forwarding. For example, the relay system may be embodied in a cell phone which communicates with the wearable monitor using the body-coupled communication system, when available. However, when the cell phone is separated from the patient, e.g. while recharging, the short range radio communication system is used.

The wearable monitor 70 and the relay system 72 automatically manage their communication by regular checking both communication links and ensuring that at least one communication link is available at any point in time. If no communication link is available, an automatic warning/notification can be communicated.

Figure 6:
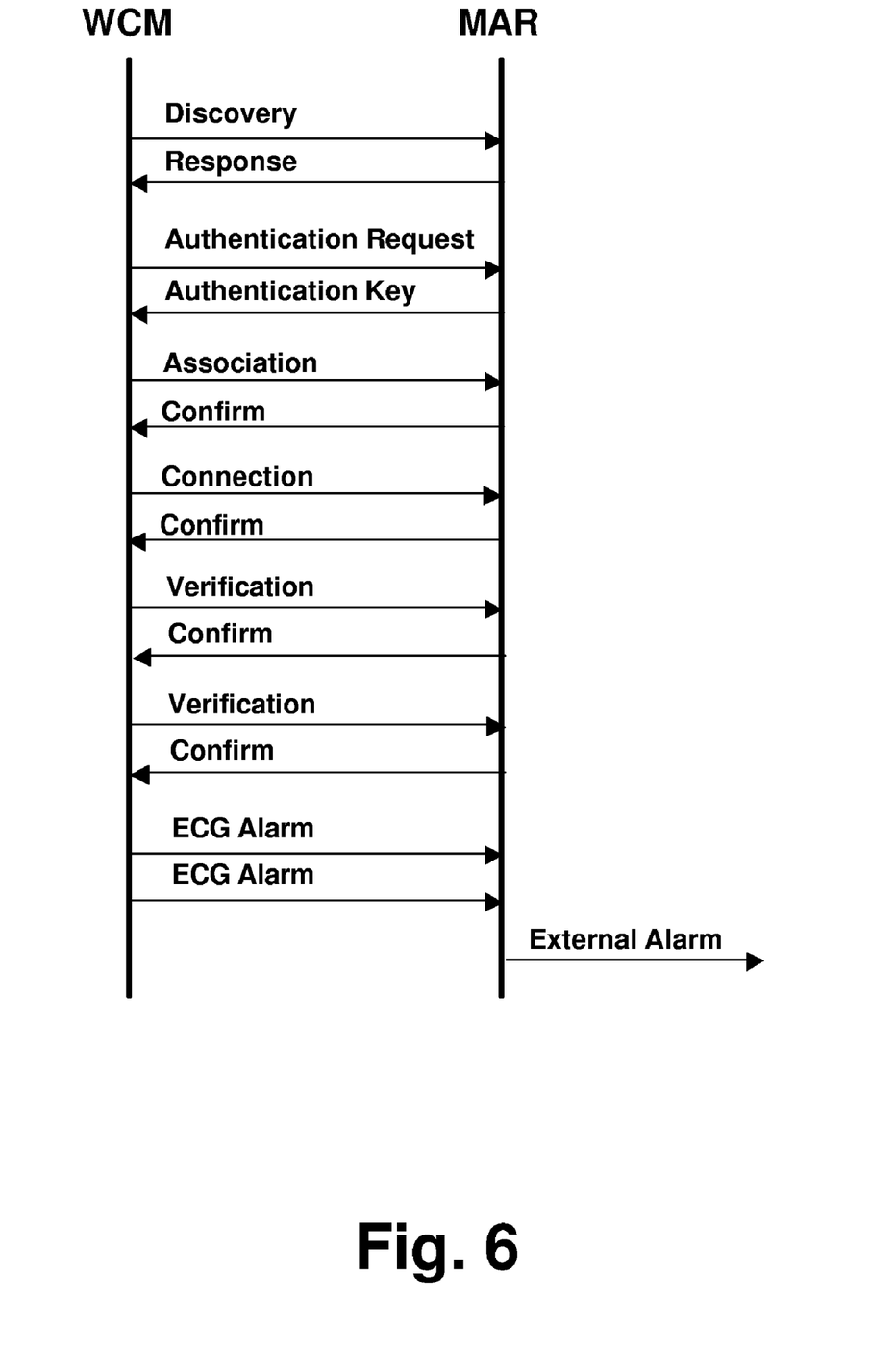
FIG. 6 shows a protocol employed in FIG. 5 to facilitate redundant communication between the wireless sensor and the relay component utilizing body coupled communication technology and radio frequency technology.

FIG. 6 illustrates the communication protocol flow between the wearable monitor 70 and the relay system 72 from FIG. 5. This communication can be broken down into three stages: association, verification and alarming. During the association phase, the BCUs 78, 80 related to the wearable monitor 70 and the relay system 72 discover each other via the body coupled communication network. A discovery signal is transmitted from the wearable monitor 70 to the relay system 72. A shared authentication key is exchanged between the wearable monitor 70 and the relay system 72 to establish secure communication between the wearable monitor 70 and the relay system 72. An authentication request signal is sent from the wearable monitor 70 to the relay system 72 and the relay system 72 returns an authentication key signal to the wearable monitor 70.

In this embodiment, there are two stages of association of the wearable monitor 70 and the relay system 72. First, BCUs 78, 80 of wearable monitor 70 and IRC (not shown) are connected. An association signal is sent via body coupled communication from the wearable monitor 70 to the relay system 72 and a confirm signal is returned from the relay system 72 to the wearable monitor 70 via body coupled communication. Second, an additional RF connection is established between the wearable monitor 70 and the relay system 72. A connection signal is sent via RF from the wearable monitor 70 to the relay system 72. The relay system 72 sends a confirm signal back to the wearable monitor 70 to indicate an RF connection is made between the wearable monitor 70 and the relay system 72.

Verification provides a regular monitoring of connections (body coupled and RF) between the wearable monitor 70 and the relay system 72. The system is notified if there is a failure of communication with either the body coupled communication or the RF connection. For both the body coupled communication and the RF connection, a verification signal is sent from the wearable monitor 70 to the relay system 72. The relay system 72 returns a confirm signal to the wearable monitor 70 to verify communication.

Alarming is provided utilizing both the body coupled communication and the RF connection. In case an ECG alarm is detected by the wearable monitor 70, an alarm message is transferred to the relay system 72. In addition to the alarm signal, ECG data can be transferred to the relay system 72. Both connection technologies, body coupled and RF, are employed in parallel to ensure connectivity. An ECG alarm signal is sent from the wearable monitor 70 utilizing both body coupled communication and an RF connection. After the relay system 72 receives at least one of the communicated ECG alarm signals, an external alarm signal is relayed from the relay system 72 to an external component via a cellular network.

In another variation, the wearable monitor 70 or the relay unit 72 connects with any nearby cell phone that is equipped to receive the signal. This assures that the alarm communication reaches the remote medical monitoring station even if the patient's cell phone is unavailable, e.g. dead battery, left out of range, etc.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A wireless network for monitoring a patient, the wireless network comprising:
    at least one wearable monitor including:
        a physiological condition sensor coupled to the patient to sense and communicate physiological data related to one physiological function of the patient,
        a first body communication unit that interfaces with the physiological condition sensor to communicate the physiological data over the patient utilizing a near field capacitive body coupled protocol, and
        a low power radio frequency transmitter; and
    a relay system including:
        a second body communication unit that receives data from and communicates with the first body communication unit utilizing the near field capacitive body coupled protocol, and
        a cell phone, the cell phone including the second body communication unit which receives the physiological data transmitted with the body coupled protocol when the cell phone is touching or closely adjacent the patient and a radio frequency receiver which receives the physiological data directly from the wearable monitor low power radio frequency transmitter when the second body communication unit is not touching or closely adjacent the patient, the cell phone communicating the physiological data over a cell phone network or internet to a remote medical monitoring station.

2. The wireless network according to claim 1, wherein the physiological condition sensor is one of heart rate, pulse oximetry, respiratory rate, blood pressure, temperature and electrocardiographic activity.

3. The wireless network according to claim 1, wherein the at least one wearable monitor and the relay system include one or more processors programmed to:
    associate the at least one wearable monitor with the relay system utilizing the near field capacitive body coupled communication protocol; and,
    verify the communication between the wearable monitor and the relay system.

4. The wireless network according to claim 3, wherein the wireless network further includes:
    an identification component that provides a unique patient identifier with the data.

5. The wireless network according to claim 1, the at least one wearable monitor further includes:
    an alarm sensor that interfaces with the physiological condition sensor to detect whether the sensed physiological condition is outside of a predetermined threshold and causes the first communication unit to send out a physiological condition message; and
    the one or more processors are further programmed to:
        cause the first body communication unit to transmit the physiological condition alarm message using the capacitive body coupled protocol to the cell phone when the cell phone via the near field capacitive body coupled communication protocol is available; and
        transmit the physiological condition alarm message by radio frequency when the cell phone communication between the wearable monitor and the cell phone via the near field capacitive body coupled communication protocol is not available.

6. The wireless network according to claim 5, wherein the at least one processor is further programmed to associate the at least one wearable monitor by:
    initializing communication between the first body communication unit associated with the wearable monitor and the second body communication unit associated with the relay system utilizing the near field capacitive body coupled protocol, and
    establishing secure communication between the wearable monitor and the mobile alarm relay system by sending an authentication request from the wearable monitor to the mobile alarm relay system and returning an authentication key from the mobile alarm relay system to the wearable monitor.

7. The wireless network according to claim 6, wherein the at least one processor is further programmed to verify the communication by:
    monitoring the connection between the wearable monitor and the mobile alarm relay system, and
    generating a connection failure alarm if the connection becomes inactive.

8. The wireless network according to claim 7, the at least one wearable monitor further includes:
an alarm sensor that interfaces with the physiological condition sensor to detect whether the sensed physiological condition is outside of a predetermined threshold and causes the first body communication unit to send out a physiological condition alarm message and the one or more processors are further programmed to:
transmit the physiological condition alarm message from the first body communication unit to the second body communication unit,
with the cell phone, send the physiological condition alarm message over the cell phone network or the interne to the remote medical monitoring station.

9. A wireless network for monitoring a patient, the wireless network comprising:
at least one wearable monitor including:
a physiological condition sensor coupled to the patient to sense and communicate data related to one physiological function of the patient, and
a first body communication unit that interfaces with the physiological condition sensor to communicate over the patient utilizing a near field capacitive body coupled protocol; and
a relay device placed on the patient including:
a second body communication unit that receives data from and communicates with the first body communication unit utilizing the near field capacitive body coupled protocol, and
an external communication unit which communicates the data to a remote medical monitoring station; and
the at least one of the wearable monitor and the relay device including at least one processor unit programmed to:
associate the wearable monitor with the relay device including:
initializing communication between the first body communication unit associated with the wearable monitor and the second body communication unit associated with the relay device utilizing the near field capacitive body coupled protocol, and
establishing a secure communication link between the wearable monitor and the device by sending an electronic authentication request from the wearable monitor to the relay device and returning an authentication key from the relay device to the wearable monitor via the near field capacitive body coupled protocol;
verifying the secure communication link between the wearable monitor and the relay device is active including:
monitoring the secure communication link between the wearable monitor and the wearable relay device, and
generating an alarm in response to the monitored secure communication link becoming inactive; and
triggering an alarm in response to the data communicated by the wearable monitor being outside of a predetermined threshold including:
communicating an alarm message from the wearable monitor to the relay device via the secure communication link, and
relaying the alarm message from the wearable relay device to the remote monitoring station;
wherein the wireless network further includes:
an identification component that provides a unique patient identifier with the data, the identification component communicating with the wearable monitor and the relay device using the near field capacitive body coupled protocol.

10. The wireless network according to claim 9, wherein the relay device includes a cell phone or PDA which receives near field capacitive body coupled communications from the wearable monitor when the cell phone or PDA is touching or closely adjacent the patient.

11. A wireless network for monitoring a patient, the wireless network comprising:
at least one wearable monitor including:
a physiological condition sensor coupled to the patient to sense and communicate data related to one physiological function of the patient,
a first body communication unit that interfaces with the physiological condition sensor to communicate data related to a physiological function of the patient over the patient utilizing a near field capacitive body coupled protocol, and
a first radio frequency transmitter to communicate data related to the physiological function of the patient in a first radio frequency signal, and
a relay system including:
a second body communication unit that receives the data from and communicates with the first body communication unit utilizing the near field capacitive body coupled protocol, and
a second radio frequency transmitter that transmits the data related to the physiological function of the patient received by the second body communication unit in a second radio frequency signal;
a cell phone or PDA unit which includes a receiver which receives the first and second radio frequency signals from the first and second radio frequency transmitters and retransmits the data on a cell phone network or the internet to a remote medical monitoring station; and
wherein the wearable monitor further includes a unit which causes the data related to one physiological function of the patient to be communicated only via the near field capacitive body coupled protocol when communication between the first and second body communications units has been established and causes the first radio frequency transmitter to communicate the data related to the physiological function of the patient when communication between the first and second body communication units is not available.

12. The wireless network according to claim 11, wherein the at least one wearable monitor and the relay system include one or more processors programmed to:
associate the at least one wearable monitor with the relay system including:
initializing communication between the first body communication unit associated with the wearable monitor and the second body communication unit associated with the relay system utilizing the near field capacitive body coupled protocol, and
establishing secure communication between the wearable monitor and the relay system by sending an authentication request from the wearable monitor to the relay system and returning an authentication key from the relay system to the wearable monitor;
verify the communication between the wearable monitor and the relay system is active including:
monitoring the connection between the wearable monitor and the relay system, and enabling the first radio frequency transmitter to communicate the data related to one physiological function of the patient if the connection becomes inactive.

13. The wireless network according to claim 12, wherein the wireless network further includes:
an identification component that provides a unique patient identifier with the data.

14. A method for transmitting patient physiological data across a wireless network, comprising:
associating a wearable monitor with a mobile alarm relay system;
coupling the wearable monitor having both radio frequency communication and near-field capacitive body coupled communication capabilities to a patient;
monitoring a physiological condition of the patient and generating an alarm when the monitored physiological condition is outside a preselected threshold via the wearable monitor coupled to the patient;
establishing a radio frequency connection between the mobile alarm relay system and an external communication unit;
providing a near-field capacitive body coupled communication link between the wearable monitor and the mobile alarm relay system;
verifying whether the near-field capacitive body coupled communication link between the wearable monitor and the mobile alarm relay system is active;
when the near-field capacitive body coupled communication link between the wearable monitor and the mobile relay system is verified as being active, transmitting the alarm from the wearable monitor to the mobile alarm relay system via the near-field capacitive body coupled communication link and from the mobile alarm relay system to the external communication unit; and
when the near-field capacitive body coupled communication link between the wearable monitor and the mobile relay system is not verified as being active, communicating the alarm from the wearable monitor directly to the external communication unit utilizing the radio frequency communication capability.

15. The method according to claim 14, wherein communicating the alarm includes:
communicating the alarm from the wearable monitor via a first body communication unit that communicates over the patient utilizing a near field capacitive body coupled protocol;
with the mobile alarm relay system, receiving the alarm from the wearable monitor utilizing the near field capacitive body coupled protocol; and
transmitting the alarm from the mobile alarm relay system to the external communication unit over the internet or a cell phone network.

16. The method according to claim 14, wherein the physiological is condition is one of heart rate, pulse oximetry, respiratory rate, blood pressure, temperature and electrocardiographic activity.

17. A method for transmitting medical information within a wireless network, comprising:
associating a wearable monitor with a mobile alarm relay system including:
initializing communication between a first body communication unit associated with the wearable monitor and a second body communication unit associated with the mobile alarm relay system utilizing a near field capacitive body coupled protocol, and
establishing a secure communication link between the wearable monitor and the mobile alarm relay system by sending an electronic authentication request from the wearable monitor to the mobile alarm relay system via the near field capacitive body coupled protocol and returning an electronic authentication key from the mobile alarm relay system to the wearable monitor via the near field capacitive body coupled protocol,
providing a unique patient identifier with the data using an identification component communicating with the wearable monitor and the relay device using the near field capacitive body coupled protocol, and
communicating with the wearable monitor and the relay device using the near field capacitive body coupled protocol;
verifying the communication between the wearable monitor and the mobile alarm relay system is active including:
monitoring the secure communication link between the wearable monitor and the mobile alarm relay system, and
generating an alarm if the secure communication link becomes inactive; and
triggering an alarm if the data transmitted by the wearable monitor is outside of a predetermined threshold including:
transmitting an alarm message from the wearable monitor to the mobile alarm relay system, and
relaying the alarm message from the mobile alarm relay system to an external network.

* * * * *